US009381134B2

(12) United States Patent
Rettinghaus et al.

(10) Patent No.: US 9,381,134 B2
(45) **Date of Patent: *Jul. 5, 2016**

(54) BLOOD PLASMA COLLECTING FLASK

(71) Applicant: Octapharma Plasma GmbH, Langenfeld (DE)

(72) Inventors: Reinhard Rettinghaus, Siegburg (DE); Hubert Franzaring, Solingen (DE); Uwe Taborski, Bad Nauheim (DE); Jürgen Schulz, Jesterburg (DE)

(73) Assignee: Octapharma Plasma GmbH (DE)

( * ) Notice: Subject to any disclaimer, the term of this patent is extended or adjusted under 35 U.S.C. 154(b) by 184 days.

This patent is subject to a terminal disclaimer.

(21) Appl. No.: 14/360,146

(22) PCT Filed: Nov. 15, 2012

(86) PCT No.: PCT/EP2012/072764
§ 371 (c)(1),
(2) Date: May 22, 2014

(87) PCT Pub. No.: WO2013/076007
PCT Pub. Date: May 30, 2013

(65) Prior Publication Data

US 2014/0324011 A1 Oct. 30, 2014

(30) Foreign Application Priority Data

Nov. 22, 2011 (DE) ..................... 20 2011 052 056 U

(51) Int. Cl.

| | |
|---|---|
| ***A61B 19/00*** | (2006.01) |
| ***A61J 1/14*** | (2006.01) |
| ***A61J 1/05*** | (2006.01) |
| ***A61J 1/12*** | (2006.01) |

(52) U.S. Cl.
CPC *A61J 1/1443* (2013.01); *A61J 1/05* (2013.01); *A61J 1/12* (2013.01); *A61J 1/1412* (2013.01);
(Continued)

(58) Field of Classification Search
CPC . A61J 2001/145; A61J 1/1475; A61J 1/1487; A61M 5/165
USPC .................................................. 604/403, 405
See application file for complete search history.

(56) References Cited

U.S. PATENT DOCUMENTS 4,568,345 A 2/1986 Keilman et al.
5,132,026 A 7/1992 Baluyot et al.
(Continued)

FOREIGN PATENT DOCUMENTS

DE 202007012912 12/2007
DE 202009001068 4/2009
(Continued)

*Primary Examiner* — Leslie Deak
(74) *Attorney, Agent, or Firm* — Berenato & White, LLC

(57) ABSTRACT

A blood plasma collecting flask consisting of plastic for storing blood plasma in a frozen state, comprising a flask body (1), which has a flask neck (2) on the upper face thereof, wherein connection points (7*a*, 7*b*) having connection pieces (8) are provided on the upper face of the flask body (1) on opposite sides of the flask neck (2) and laterally spaced apart from same, of which connection points one connection point (7*a*) is used to fill the flask body (1) with blood plasma and the other connection point (7*b*) is used for taking samples, and substantially L-shaped connectors (9) are provided at the connection points (7*a*, 7*b*), wherein each connector limb is connected to the connection piece (8) of the flask body (1) and the other connector limb points towards the flask neck (2) and bears a tube (10).

9 Claims, 12 Drawing Sheets

(52) U.S. Cl.
CPC ................ *A61J 1/1475* (2013.01); *A61J 1/145* (2015.05); *A61J 1/1456* (2015.05); *A61J 1/1487* (2015.05); *A61J 1/2068* (2015.05)

(56) References Cited

U.S. PATENT DOCUMENTS 5,728,086 A 3/1998 Niedospial
8,834,435 B2 * 9/2014 Rettighaus ................ A61J 1/05
604/317
2010/0030181 A1 * 2/2010 Helle .................... A61M 5/162
604/411

FOREIGN PATENT DOCUMENTS

EP 1002512 5/2000
EP 2433608 3/2012

* cited by examiner

BLOOD PLASMA COLLECTING FLASK

CROSS-REFERENCE TO RELATED APPLICATIONS AND CLAIM TO PRIORITY

This application is a national stage application of International Application No. PCT/EP2012/072764 filed Nov. 15, 2012, which claims priority to German Patent Application No. 20 2011 052 056.0 filed Nov. 22, 2011, of which the disclosures are incorporated herein by reference and to which priority is claimed.

FIELD OF THE INVENTION

The present invention relates to a blood plasma collecting flask made of plastic for the storage of blood plasma in the frozen state, comprising a flask body which has on its upper side a flask neck.

BACKGROUND OF THE INVENTION

Blood plasma collecting containers in the form of plastic bags have been known for many years and have proved to be of value when freezing by the use of materials such as ethylene vinyl acetate (EVA) and polyethylene (PE). The disadvantage of blood plasma collecting containers in the form of blood bags is poor manageability because they can not be set down without any auxiliary means or special structures, and there is moreover the risk of them being damaged in the frozen state by falling down. Moreover, they bulge out uncontrollably, and so it is difficult to control the filling quantity.

For this reason it is proposed in DE 20 2007 012 912 U1 to use blood plasma collecting flasks made of plastic, the flask body of which has in the horizontal section a cross-section with a rectangular basic shape, and has on its upper side a flask neck closed by a covering plate. Two connection points are provided on the covering plate, of which one connecting point is provided for the filling of the flask body with blood plasma, and the other connection point is used for ventilation and taking samples. A lid can be fixed onto the covering plate in order to protect the connection points. This cover has two slots which are used for passing through tubes fixed to the connection points.

During the plasma donation the lid is located in a position in which the tubes are passed through the slots unhindered. Once the plasma donation is complete the tubes are cut off and sealed. In order to fix the free ends of the cut-off tubes the lid is turned by means of which the free ends are drawn into the lid.

The known blood plasma collecting flask has proved to be of value in practice, but endeavours are being made to further improve functionality and manageability.

SUMMARY OF THE INVENTION

Therefore, it is the object of the present invention to design a blood plasma collecting flask made of plastic for storing plasma in the frozen state of the type specified at the start so that its manageability is improved. Its dimensional stability in particular should thus be improved and its handling simplified.

According to the present invention this object is solved in that connection points with connection ports are provided on the upper side of the flask body on opposite sides of the flask neck and spaced apart from the latter to the side, wherein one connection point is used for filling the flask body with blood plasma and the taking of samples and a substantially L-shaped connector is provided at this connection point, the one connector arm of which being connected to the flask body, and the other connector arm being directed towards the flask neck and bearing a tube which extends over the flask neck, and wherein the other connection point is used for ventilation, a preferably hydrophilic sterile filter being provided at the connection point.

According to the present invention one connection point is designed to serve for filling the flask body with blood plasma and the taking of samples. At this connection point an L-shaped connector is provided, the one connector arm of which is directed towards the flask neck. The other connection port is used solely for ventilation when filling with blood plasma and for ventilation during the taking of samples, so that both operations can be carried out easily. This connection port is provided with a preferably hydrophilic sterile filter. This can be inserted into the connection port.

The L-shaped connector is attached to the connection port in an releasable manner. For example the connectors can be glued or welded to the connection ports. Preferably they are, however, attached to the connection ports by means of a latch connection in an unreleasable and self-sealing manner. For this purpose sealing faces corresponding to one another can be formed on the connection ports and the L-shaped connector, that come into contact with each other under pressure, when the L-shaped connectors are fixed to the connection ports. The sealing faces can for example be provided on the upper edge of the connection ports and a corresponding ring face at the inner side of the connectors.

On the tube, that is connected with the connection point, which is used for the taking of samples, usually a sample tube or pilot tube is attached. According to one embodiment of the present invention the tube carries on its one end at least one pilot bag, wherein the pilot bag has a ventilation opening, in which is provided a hydrophilic frit. In this embodiment the taking of samples is carried out in a simple manner in that the blood plasma connection flask is tilted, so that a fluid flows from the flask into the pilot bag. Subsequently the pilot bag is closed by welding its end facing to the flask. Moreover the ventilation opening is closed. The later is preferably formed in a tubular welding end of the pilot bag, in which also a hydrophilic frit is positioned, so that the ventilation opening can also be closed by welding the welding end.

In a preferred way to pilot bags are connected with the tube that is connected with the connection point for the ventilation and the taking of samples via a corresponding, in particular Y-shaped connection tube. In the embodiment, in which one connection point servers for filling the flask body with blood plasma as well as the taking of samples, the tube connected to the respective connector must be branched, wherein the one free end is to be connected with the blood plasma pheresis apparatus and on the other free hand the pilot tubes or pilot bags are connected.

In a way known in its own right a lid can be fixed or is fixable to the flask neck, and in particular to a covering plate closing the flask neck on its upper side. Said lid is designed such that in the fixed state it overlaps the sections of the tubes projecting over the flask neck and positions them thus. The lid can be designed in such that in the fixed stated overlaps the connection points and thus protects them from outer access.

In the design of the invention provision is made such that the lid has notches assigned to the connectors tubes and open towards the lower side of the lid which engage with the tube sections projecting over the flask neck and are passed through by said tube sections when the lid is fixed onto the flask neck.

In addition the lid can have on the inside holding bars which overlap and position the tubes when the lid is fixed onto the flask neck.

Preferably a locking mechanism is provided by means of which the lid is fixed onto the flask neck and in particular onto the covering plate when the lid is pushed onto the flask neck from above. Here, according to a further aspect of the invention the locking mechanism has a first locking position in which the lid can be released again from the flask neck, and a second locking position in which the lid is pushed further onto the flask neck than in the first locking position and in which the lid is prevented from being released from the flask neck. With this embodiment the lid is attached releaseably to the flask neck in the delivery state, i.e. it is engaged in the upper, first locking point. It is thus possible to release the lid from the flask neck in order to fill the blood plasma collecting flask and then to seal off the connectors. After sealing off the lid is then finally fixed onto the flask neck by bringing it into the second locking position in which it is no longer possible to release it.

In the configuration of this embodiment provision can be made such that lugs are formed on the lower, open lid edge which, upon pushing the lid onto the flask neck, engage with a holding bar formed on the flask neck, and in particular onto the outer edge region of the covering plate, are elastically expanded, and when pushed on further spring back elastically and engage behind the holding bar thus establishing the first locking position.

Furthermore, provision can be made such that on the upper side of the flask neck and in particular on the covering plate, a bar projecting uprightly and on the inside of the lid a retainer corresponding to the bar are formed which engage with one another when the lid is pushed onto the flask neck, and such that locking elements of the locking mechanism are formed on the bar and the retainer which engage with one another in the second locking position.

Here a locking opening can be formed in the bar in which a locking element provided on the retainer side engages in the second locking position.

According to a further embodiment, holding elements, in particular holding clips, can be provided on the lid, and in particular on the upper side of the lid, for releaseably attaching test tubes. This embodiment makes it possible to supply the test tubes as a unit with the blood plasma collecting flask.

According to a further design of the blood plasma collection flask according to the present invention the lateral faces of the flask body respectively define a flat or slightly inwardly curved area adjoining which are areas rounded towards the face surfaces. It has been shown that flask bodies formed in this way are particularly dimensionally stable. This is particularly the case if the areas are curved slightly inwards, the curvature having a maximum depth of 2 mm, in particular of 1.5 mm, in relation to the edges of the curvature. By means of the inwardly directed curvature a type of pre-stressing is achieved which counters bulging out of the flask body when filling. The stability of the flask is further increased if the flat or slightly inwardly curved areas have a hexagonal form the base sides of which lie on the crossover areas of the lateral faces to the upper side and lower side of the flask body and preferably are uniformly hexagonal in form such that the corners lying between the base sides are positioned approximately half way up the flask body. The flask body then has a form which is obtained if one presses an oval or round body flat, in this case the sides of the hexagonal surfaces lying between the base sides being slightly rounded.

Furthermore the flask body can have a number of reinforcing ridges that extend around the flask body and are preferably positioned such that they act at least partially as filling height indicators. Preferably a total of four reinforcing ridges are formed on the flask body, in particular two reinforcing ridges being provided in the upper half of the flask body and two reinforcement ridges being provided in the lower half of the flask body.

BRIEF DESCRIPTION OF THE FIGURES

With regard to further advantageous embodiments of the invention reference is made to the sub-claims and to the following description of an exemplary embodiment with reference to the attached drawings. The drawings show as follows:

DETAILED DESCRIPTION OF THE PREFERRED EMBODIMENT(S)

Figure 1:
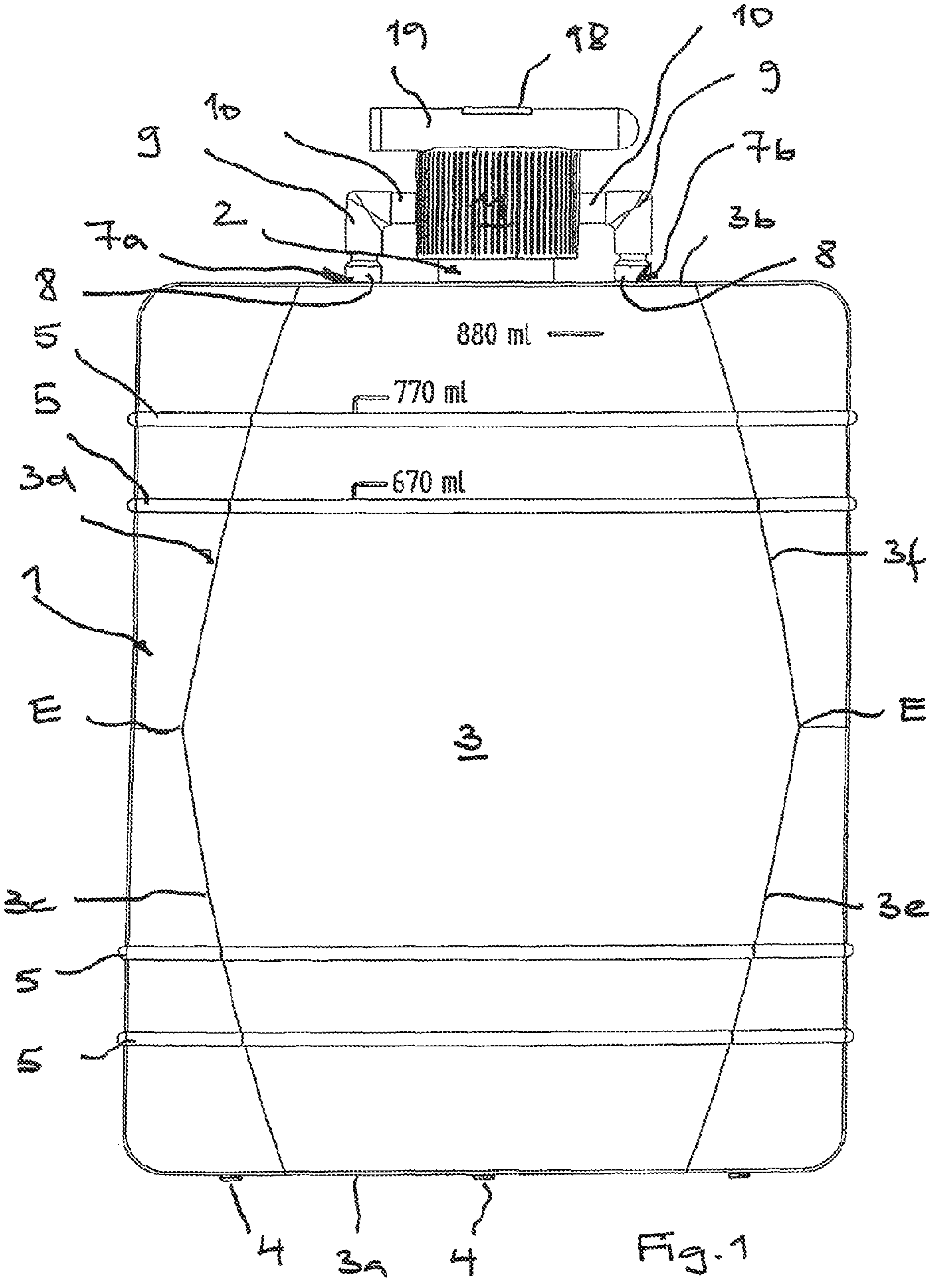
FIG. 1 a front view of a blood plasma collecting flask according to the present invention.
Figure 2:
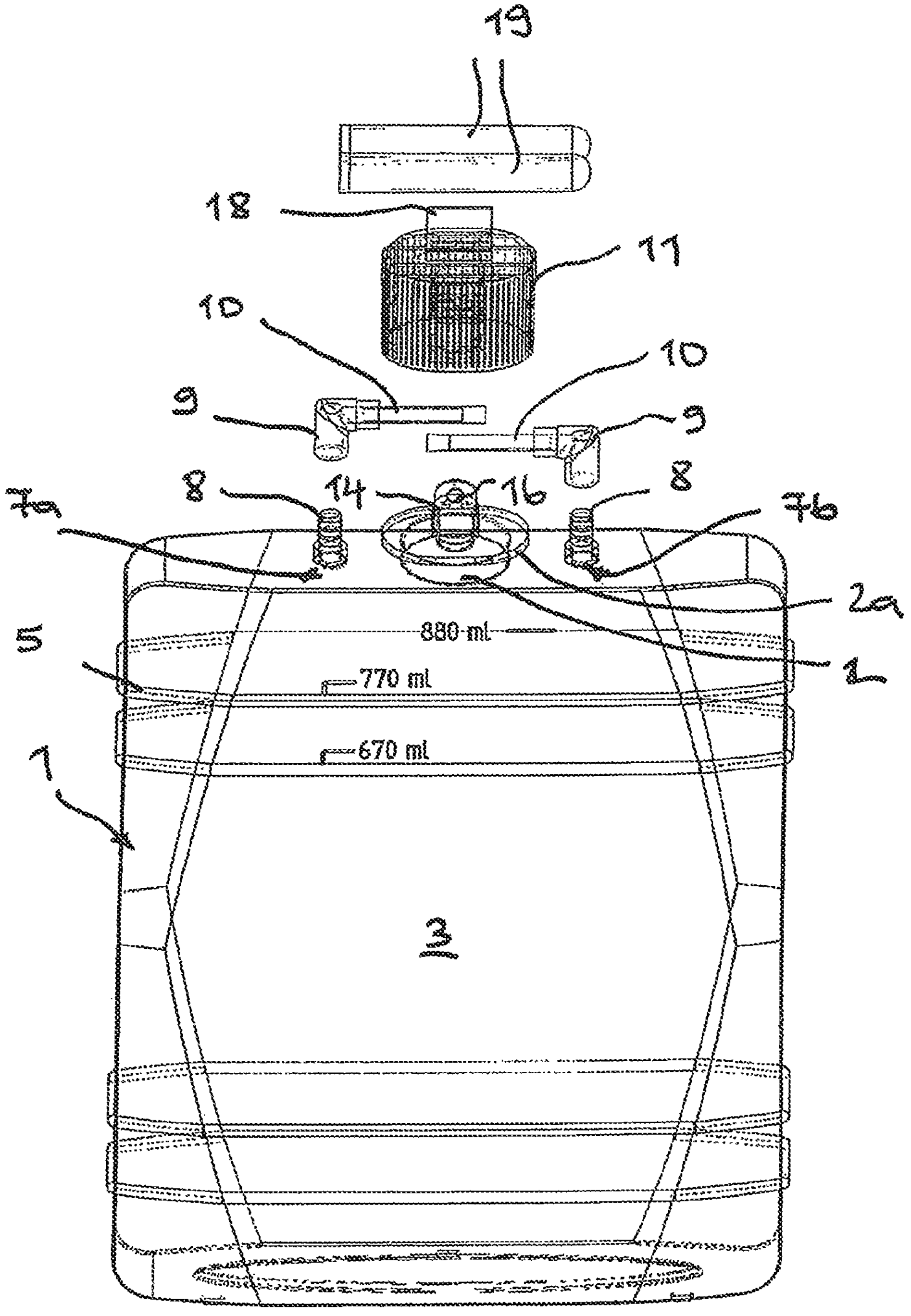
FIG. 2 a perspective exploded view of the blood plasma collecting flask from FIG. 1.
Figure 3:
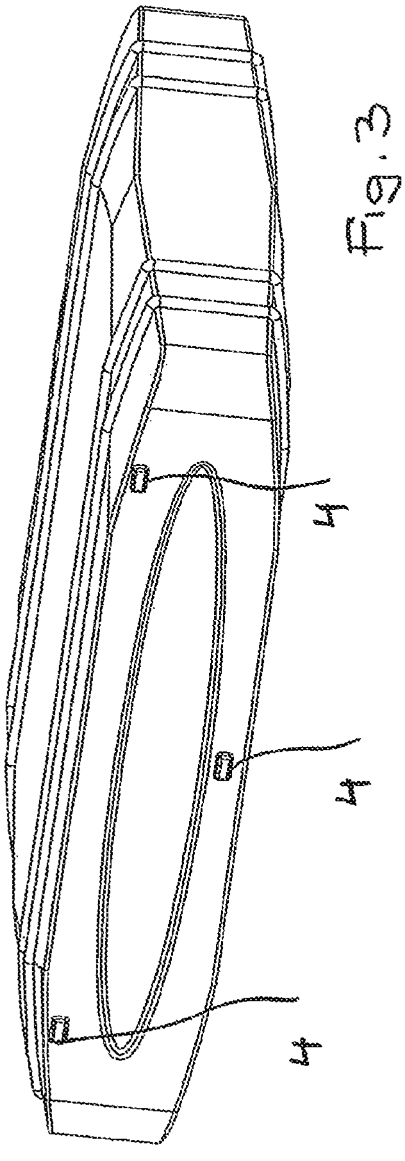
FIG. 3 a perspective illustration of the blood plasma collecting flask from FIG. 1 viewed from below at an angle.
Figure 4:
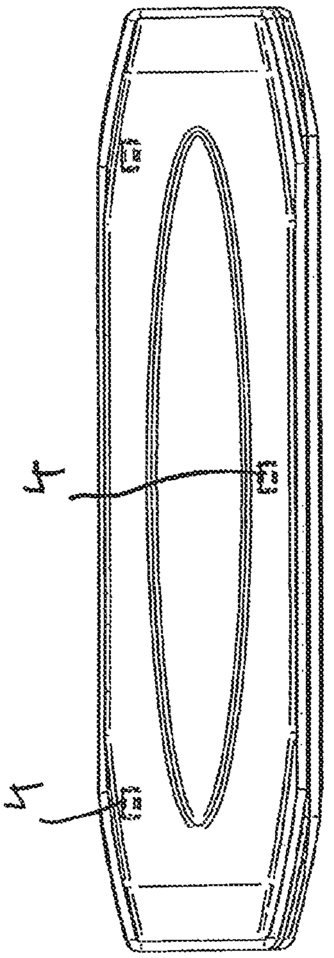
FIG. 4 the blood plasma collecting flask from FIG. 1 viewed from below.
Figure 5:
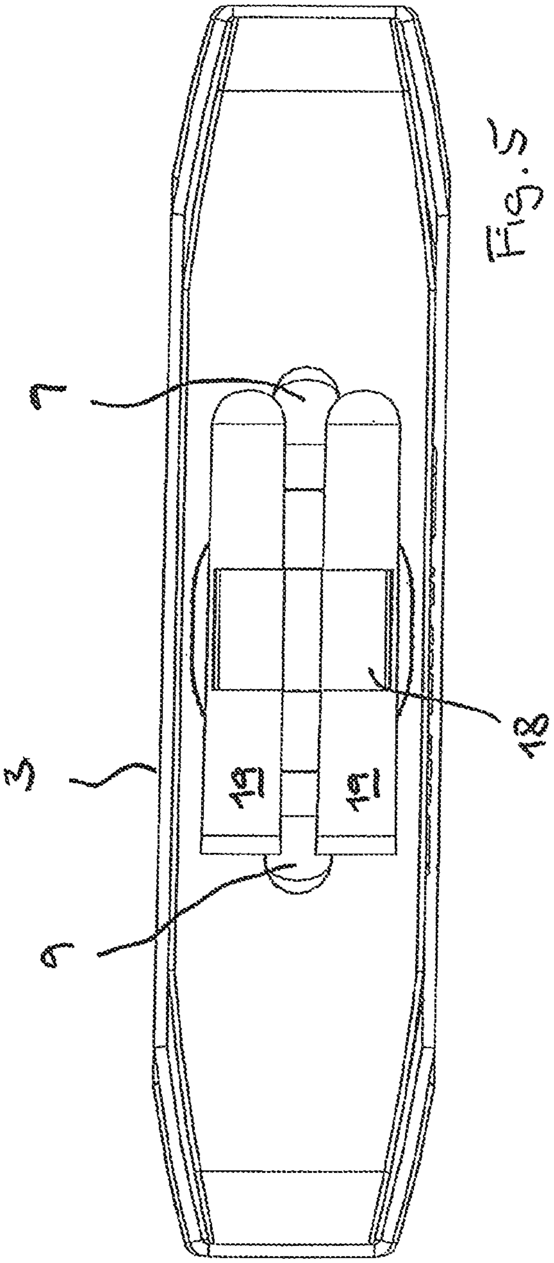
FIG. 5 a top view of the blood plasma collecting flask from FIG. 1.

The drawings illustrate a blood plasma collecting flask for storing blood plasma in the frozen state according to the present invention. The blood plasma collecting flask is made of plastic, in particular of polyethylene (PE), and has a flask body 1 which in the horizontal section has a cross-section with a rectangular basic shape, and on its upper side bears a flask neck 2 with a covering plate 2*a* provided on the upper side. As can be seen well in the drawings the lateral faces of the flask body 1 respectively define a flat area 3 with a hexagonal form the base sides 3*a*, 3*b* of which lie on the crossover areas of the lateral faces to the upper side and lower side of the flask body 1, the corners E lying between the base sides 3*a*, 3*b* being positioned approximately half way up the flask body 1. Here the sides 3*c*, 3*d*, 3*e*, 3*f* of the hexagonal area 3 lying between the base sides 3*a*, 3*b* are slightly rounded. Adjoining the flat lateral faces of the flask body 1 are the face surfaces which are rounded in form. Overall, therefore, the flask body 1 has a form which is obtained if one pushes flat a base body which is round or oval in form. It can not be seen in the drawings that the flat areas 3 can also be curved slightly inwards, the curvature in the middle of the hexagonal area 3 having a depth of approximately 1.5 mm in relation to the edges of the hexagonal area 3. By means of this embodiment a type of pre-stressing is achieved which counters bulging out of the flask body 1 when filling with blood plasma.

Furthermore, the flask body 1 has a total of four reinforcing ridges 5 which extend around the flask body 1, two reinforcing ridges 5 being provided in the upper flask body half, and two reinforcing ridges 5 being provided in the lower flask body half. The upper two reinforcing ridges 5 act here as filling height indicators.

On the lower side of the flask body 1 three adjustable feet 4 are provided by means of which it is ensured that the flat blood plasma collecting flask can be set down stablely.

There are provided on the upper side of the flask body 1 on opposite sides of the flask neck 2 and spaced apart from the latter to the side, two connection points 7*a*, 7*b*, one connection point 7*a* of which is used for filling the flask body 1 with blood plasma, and the other connection point 7*b* is used for ventilation and for taking samples. Provided at the connection points 7*a*, 7*b* are connection ports 8 securely connected to the flask body 1 on which L-shaped connectors 9 are held non-releaseably. Alternatively, the flask body 1 may have two connection points 7*c*, 7*d*, of which the one connection point 7*c* serves for filling the flask body 1 with blood plasma as well as for the taking of samples. As can be obtained from FIG. 9 in this case only the connection port 8 of the connection point 7*c* serving for filling and taking of samples is provided with an L-shaped connector 9. The connection port 8 of the other connection point 7*d* only serves for the ventilation of the flask body 1. In this connection port 8 a hydrophilic sterile filter not shown is provided.

Figure 9:
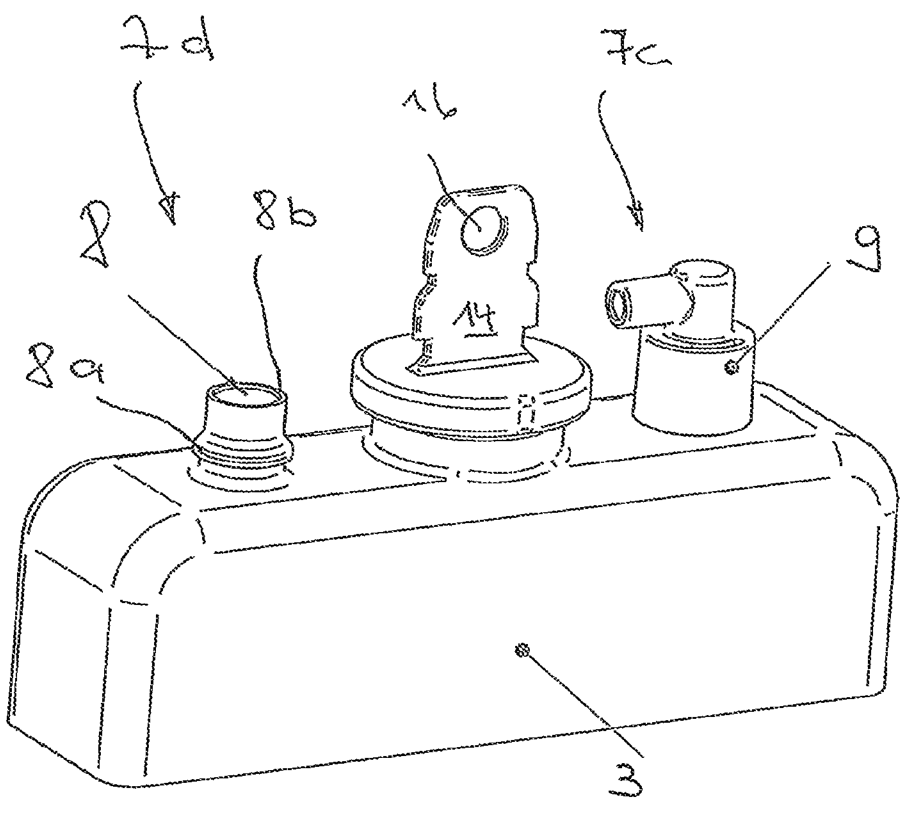
Figure 10:
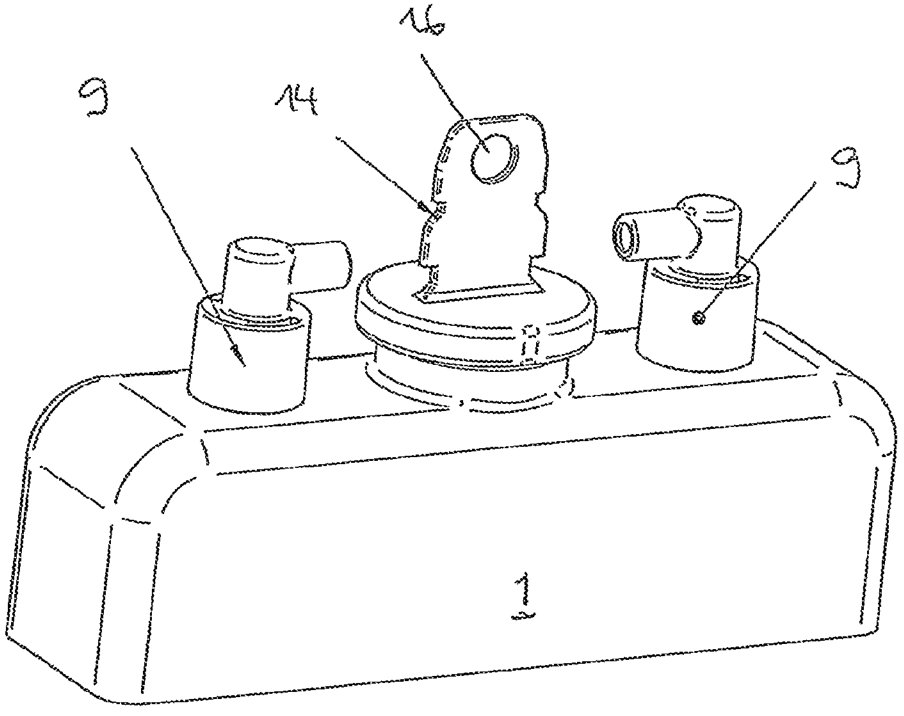
FIG. 10 the upper region of the blood plasma collecting flask with two L-shaped connectors fixed thereto.
Figure 11:
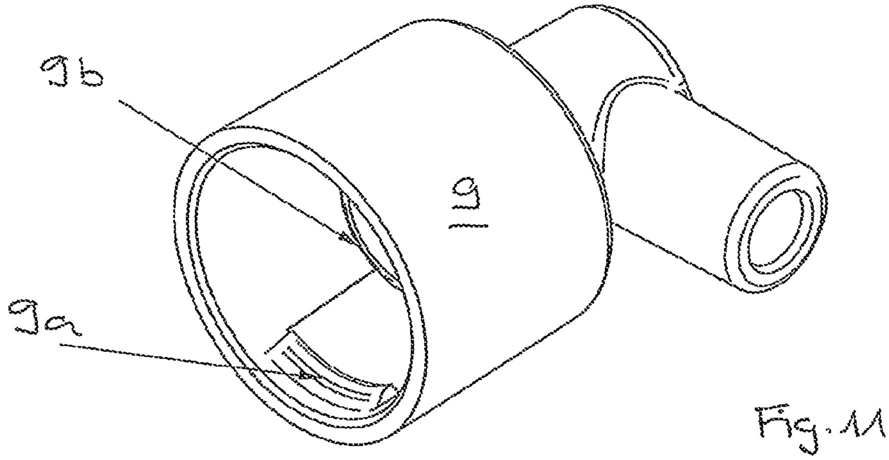
FIG. 11 an L-connector in an enlarged perspective illustration.

As is obtainable in particular from FIGS. 9 to 11 the L-shaped connectors 9 are connected to the connection ports 8 by means of a latch mechanism. For this purpose in the lower end region of the connection ports 8 a latch shoulder 8*a* extending outwardly and on the inner sides of the connectors 9 a corresponding latch nose 9*a*, which elastically engages the latch shoulder 8*a* from behind, when a connector 9 is pressed onto the connection port 8 are provided. Moreover in FIG. 11 is shown, that on the inner side of the connectors 9 a sealing face 9*a* is provided, which comes into sealing engagement under pressure with a sealing face 8*b* on the upper edge of the corresponding connection port 8, when the connector 9 is fixed to the connection port 8.

Tubes 10 are attached to the connector arms facing away from the connection ports 8. The arrangement here is such that the connector arms facing away from the connection port are directed towards the flask neck 2 so that the tubes 10 held on the latter extend over the covering plate 2*a* of the flask neck 2. In the drawings the tubes 10 are illustrated in the sealed off state in which the tube ends lie directly above the covering plate 2*a*. In the non-sealed off state the tubes 10 are clearly longer, the one tube extending to the plasmapheresis device, and the other tube bearing a ventilation opening and an apparatus for taking samples.

A lid 11 is fixed to the covering plate 2*a* of the flask neck 2. The latter is designed such that in the fixed state it overlaps the sections of the tubes 10 projecting over the flask neck 2 and protects them against access from the outside. More specifically, the lid 11 has slot-shaped notches 12 assigned to the tubes 10 and open to the lower side of the lid which engage with the tube sections projecting over the flask neck 2 and are passed through by the latter when the lid 11 is fixed by the flask neck 2.

Figure 12:
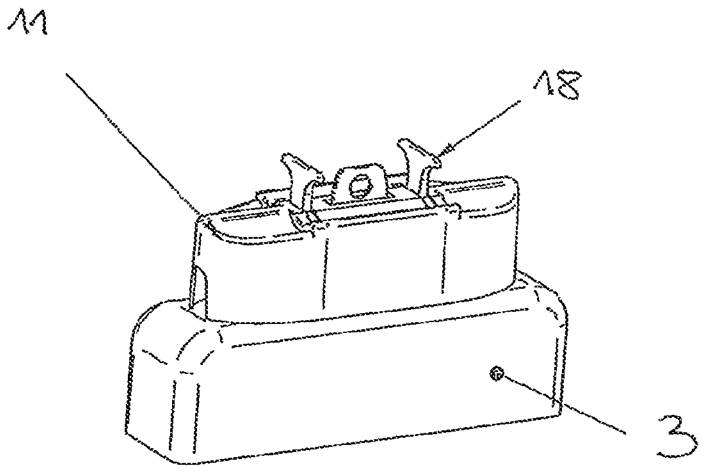
FIG. 12 the upper region of the blood plasma connecting flask with a lid fixed thereto and FIG. 13 the upper region of a blood plasma connecting flask with two pilot bags that are connected to one of the connectors.

As shown in FIG. 12 the lid 11 can be designed so broad, that it extends around the L-shaped connectors 9.

Figure 8:
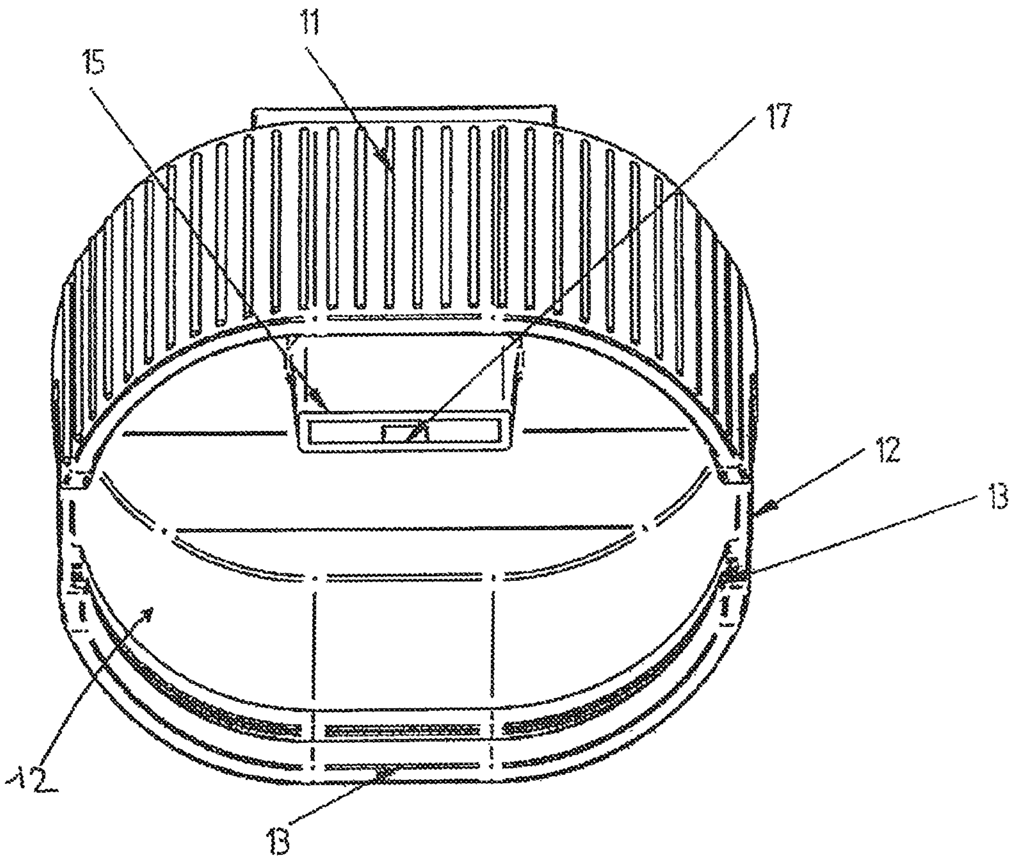
FIG. 8 a perspective illustration of the lid of the blood plasma collecting flask viewed from below at an angle, FIG. 9 a perspective enlarged illustration of the upper region of a blood plasma connecting flask having an L-shaped connector fixed thereto.

The fixing of the lid 11 to the flask neck 2 is implemented by means of a locking mechanism when the lid 11 is pushed from above onto the flask neck 2. This locking mechanism comprises a first locking position in which the lid 11 can be released again from the flask neck 2, and a second locking position in which it is essentially no longer possible to release the lid 11 from the flask neck 2. More specifically there are formed on the lower, open lid edge lugs 13 which when the lid 11 is pushed down onto the flask neck 2 engage with the outer edge region of the covering plate 2*a*, are elastically expanded, and when the lid 11 is pushed down further spring back elastically, and engage behind the covering plate 2*a* thus establishing the first locking position. In FIG. 8 it can be seen easily that the lugs 13 extend over substantially the whole lower edge region of the lid 11. The lid 11 obtains the elasticity required for expanding by means of the notches 12 for the tubes 10. The engagement between the lugs 13 and the covering plate 2*a* can be released again by the lower edge regions of the lid 11 being bent manually outwards.

Figure 6:
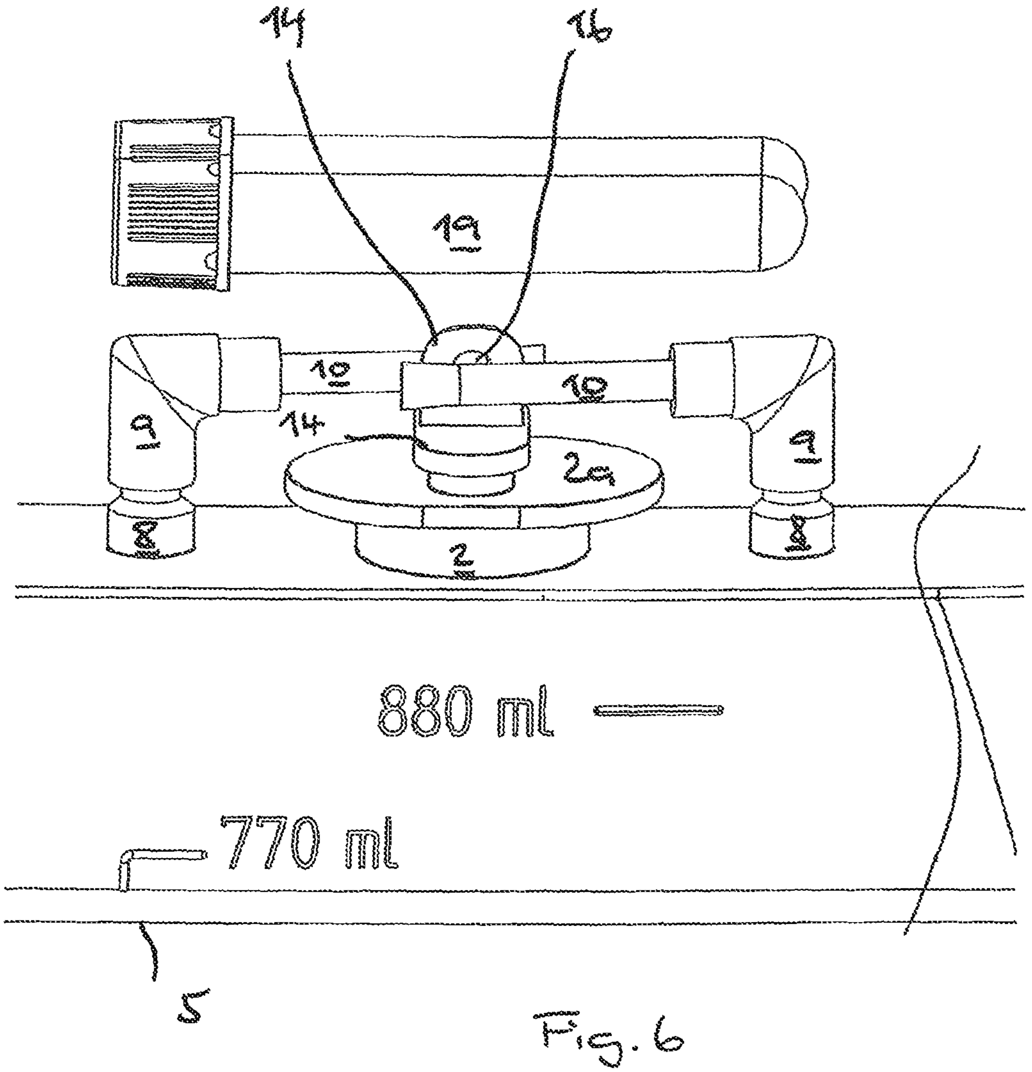
FIG. 6 an enlarged representation of the upper region of the blood plasma collecting flask with the lid removed.

Furthermore, in FIGS. 6 and 8 it can easily be seen that there are formed on the upper side of the covering plate 2*a* a perpendicularly projecting bar 14 and on the inside of the lid a retainer 15 corresponding to the bar 14 which engage with one another when the lid 11 is pushed onto the flask neck 2. A static locking opening 16 is formed here on the bar 14 with which a locking tooth 12 provided on the retainer side engages when the lid 11 is pushed via the first locking position further onto the flask neck 2 into the second locking position. The engagement area between the locking opening 16 and the locking tooth 17 is not accessible from the outside, and so this connection is prevented from being released.

Figure 7:
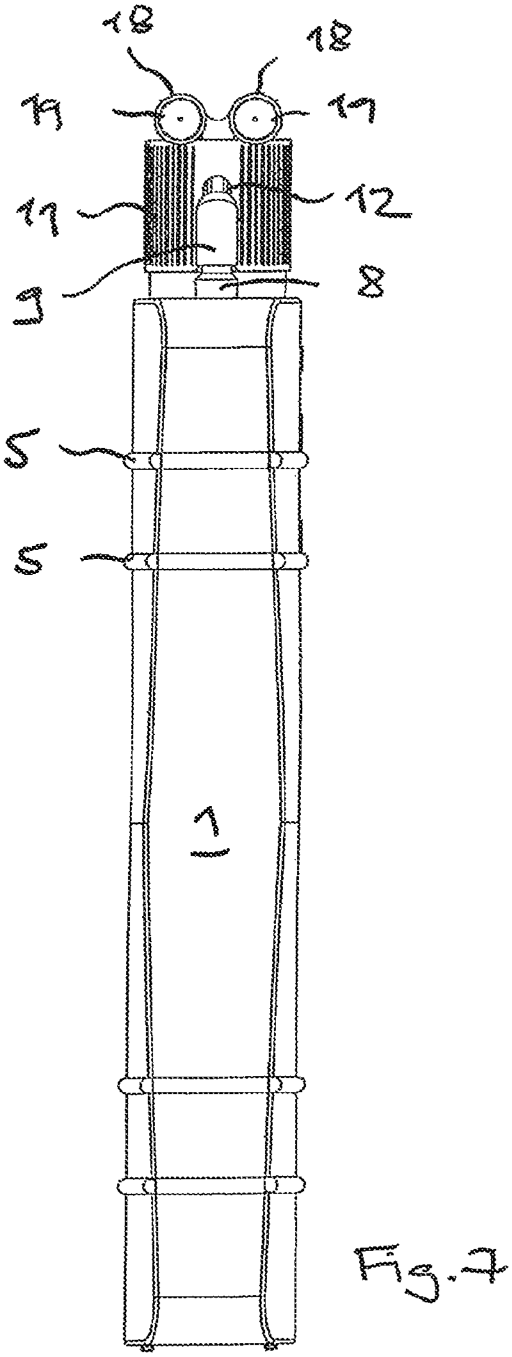
FIG. 7 a side view of the blood plasma collecting flask from FIG. 1.

Finally, it can be seen easily in FIG. 7 that the lid 11 bears on its upper side holding clips 18 for releaseably attaching test tubes 19.

In the delivery state the lid 11 is fixed by means of the upper, first locking point to the flask neck 2. After the blood plasma collecting flask has been filled in the normal way, the lid 11 is removed, and then the tubes 10 are sealed off such that there is room for them beneath the lid 11. After sealing off the lid 11 is attached again onto the flask neck 2 and pushed down here to such an extent that fixing is implemented by means of the second locking position so that the lid 11 is prevented from being removed again. The tubes 10 are thus inaccessible for subsequent manipulations.

Figure 13:
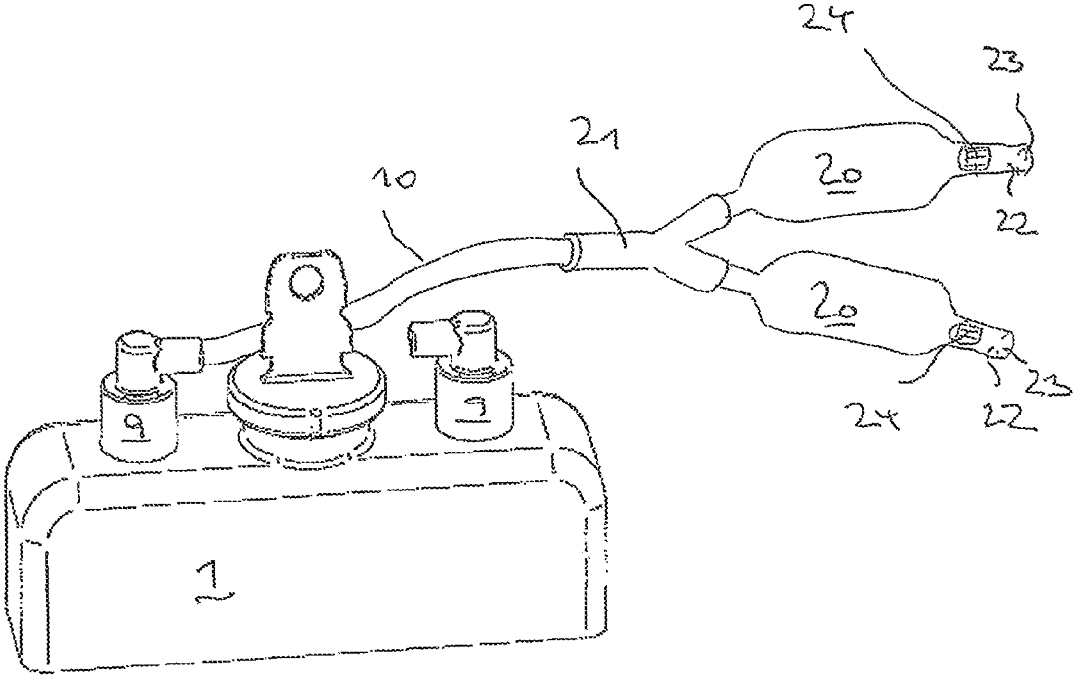

In FIG. 13 is finally shown an embodiment, wherein instead of tubes for the taking of samples two pilot bags 20 are connected with the connector 9 serving for the taking of samples. Specifically the tube 10, which is connected with the free end of the L-shaped connector 9 on the connection point 7*b* for the taking of samples, is connected at its free end via an Y-shaped connection tube 21 with two pilot bags 20. These extend sealingly with a welding end into the Y-shaped connection tube 21 and are fixedly connected to the same. At the opposite end region the pilot bags 20 comprise a tubular welding end 22 with a ventilation opening 23, wherein a hydrophilic frit 24 is provided in the welding end 22.

In this embodiment the taking of samples is effected in an easy manner by tilting the blood plasma collecting flask, so that fluid flows from the flask body 1 into the two pilot bags 20, until the hydrophilic frit 24 is closed. Subsequently the pilot bags 20 are welded on their welding ends 22.

Instead of the Y-shaped connection tube 21 a connection tube with three or more connecting ends may be provided, wherein the further connecting ends then form ventilation openings, in which hydrophilic sterile filters of frits can be provided through which during the filing of the blood plasma collecting flask air can escape from the flask body 1.

In case of a blood plasma collecting flask according to FIG. 9, wherein the filling of the blood plasma collecting flaks 1 as well as the taking of samples happens via a common connection point 7*c*, the tube 10 has a further branch, via which then the filling of the flaks may occur.

The invention claimed is:

1. A blood plasma collecting flask made of plastic for the storage of blood plasma in the frozen state, comprising a flask body (1) which has on its upper side a flask neck (2), wherein connection points (7*c*, 7*d*) with connection ports (8) are provided on the upper side of the flask body (1) on opposite sides of the flask neck (2) and spaced apart from the latter to the side, wherein one connection point (7*c*) is used for filling the flask body (1) with blood plasma and the taking of samples and a substantially L-shaped connector (9) is provided at this connection point (7*c*), the one connector arm of which being connected to the flask body (1), and the other connector arm being directed towards the flask neck (2) and bearing a tube (10) which extends over the flask neck (2), wherein the other connection point (7*d*) is used for ventilation, and wherein a hydrophilic sterile filter is provided at this connection point (7*d*).

2. The blood plasma collecting flask according to claim 1, wherein the tube (10), that is connected with the L-shaped connector (9) at the connection point (7*c*) which is used for the taking of samples carries at its free end at least one pilot bag (20) and is connected to the later, wherein the pilot bag (20) has a ventilation opening (23), in which is provided a hydrophilic frit.

3. The blood plasma collecting flask according to claim 2, wherein the pilot bag (20) has a tubular welding end (22), at the free end of which the ventilation opening (23) is provided and in which the hydrophilic frit (24) is positioned.

4. The blood plasma collecting flask according to claim 3, wherein two pilot bags (20) are connected via a corresponding, in particular Y-shaped connection tube (21) with the tube (10), that is connected with the L-shaped connector (9) of the connection port (7*c*) for the taking of samples.

5. The blood plasma collecting flask according to claim 2, wherein two pilot bags (20) are connected via a corresponding, in particular Y-shaped connection tube (21) with the tube (10), that is connected with the L-shaped connector (9) of the connection port (7*c*) for the taking of samples.

6. The blood plasma collecting flask according to claim 1, wherein at least one L-shaped connector (9) is attached to the connection port (8) by means of latch connection in an unreleasable and self-sealing manner.

7. The blood plasma collecting flask according to claim 6, wherein sealing faces (8*b*, 9*b*) corresponding to one another are formed on the connection port (8) and the L-shaped connector (9), that come into contact with each other under pressure, when the L-shaped connector (9) is fixed to the connection port (8).

8. The blood plasma collecting flask according to claim 7, wherein the tube (10), that is connected with the L-shaped connector (9) at the connection point (7*c*) which is used for the taking of samples carries at its free end at least one pilot bag (20) and is connected to the later, wherein the pilot bag (20) has a ventilation opening (23), in which is provided a hydrophilic frit.

9. The blood plasma collecting flask according to claim 6, wherein the tube (10), that is connected with the L-shaped connector (9) at the connection point (7*c*) which is used for the taking of samples carries at its free end at least one pilot bag (20) and is connected to the later, wherein the pilot bag (20) has a ventilation opening (23), in which is provided a hydrophilic frit.

* * * * *